US012765960B2

(12) United States Patent
Srivastava et al.

(10) Patent No.: US 12,765,960 B2
(45) Date of Patent: Oct. 20, 2026

(54) MULTI-ARM ROBOTIC SURGICAL SYSTEM

(71) Applicant: SSI IP HOLDINGS, INC., FL Lauderdale, FL (US)

(72) Inventors: Sudhir Prem Srivastava, Gurugram (IN); Vishwajyoti Pascual Srivastava, Gurugram (IN); Nitin Hemdan, Gurugram (IN); Suraj Dwivedi, Gurugram (IN); Rama Krishna Reddy Dyava, Gurugram (IN); Shubhankar Sanjiv Kulkarni, Gurugram (IN); Anil Kumar Patidar, Gurugram (IN); Suryanshu Sundar Chopdar, Gurugram (IN); S Naveen Ajay Kumar, Gurugram (IN); Manish, Gurugram (IN); Yogesh Singh, Gurugram (IN)

(73) Assignee: SSI IP HOLDINGS, INC., Fort Lauderdale, FL (US)

( * ) Notice: Subject to any disclaimer, the term of this patent is extended or adjusted under 35 U.S.C. 154(b) by 294 days.

(21) Appl. No.: 18/690,545

(22) PCT Filed: Oct. 20, 2023

(86) PCT No.: PCT/IN2023/050967
§ 371 (c)(1),
(2) Date: Mar. 8, 2024

(87) PCT Pub. No.: WO2024/084514
PCT Pub. Date: Apr. 25, 2024

(65) Prior Publication Data
US 2025/0127578 A1 Apr. 24, 2025

(30) Foreign Application Priority Data
Oct. 21, 2022 (IN) ............................ 202211060219

(51) Int. Cl.
*A61B 34/37* (2016.01)
*A61B 34/00* (2016.01)
(Continued)

(52) U.S. Cl.
CPC ............ *A61B 34/37* (2016.02); *A61B 90/361* (2016.02); *A61B 2034/306* (2016.02); *A61B 2034/742* (2016.02); *A61B 2090/372* (2016.02)

(58) Field of Classification Search
CPC ......... A61B 34/20; A61B 34/25; A61B 34/30; A61B 34/35; A61B 34/37; A61B 34/70;
(Continued)

(56) References Cited

U.S. PATENT DOCUMENTS

2010/0228249 A1* 9/2010 Mohr ............... A61B 1/000096 715/764
2020/0012116 A1 1/2020 Fuerst
(Continued)

FOREIGN PATENT DOCUMENTS

EP 3892227 A1 10/2021
WO 2010104753 A1 9/2010
WO 2020092170 A1 5/2020

OTHER PUBLICATIONS

Alletti, Salvatore Gueli, Introducing the New Surgical Robot Hugo™ RAS: System Description and Docking Settings for Gynecological Surgery, Frontiers in Oncology, Article 898060, vol. 12.

*Primary Examiner* — Robert A Lynch
(74) *Attorney, Agent, or Firm* — Maschoff Brennan

(57) ABSTRACT

A multi-arm robotic surgical system having an endoscopic camera (C) coupled to a robotic arm and a plurality of surgical instruments each detachably coupled to a robotic arm. The multi-arm robotic surgical system further comprises of a surgeon console having a master controller, a left-hand controller and a right-hand controller, a three-
(Continued)

dimensional (3D) HD monitor, a two-dimensional (2D) touch screen monitor, a pair of trackable 3D glasses to be worn by the surgeon, a head tracking camera, a foot pedal controller, a control panel for performing emergency system functions, an electrosurgical unit interface, an image processor configured to process a 3D image data received from the endoscopic camera (C), a digital device configured to prepare an image data by using the processed 3D image data received from the image processor and superimposing it with a 2D overlay including a status of the plurality of surgical instruments and display on the 3D HD monitor and a patient side staff 3D monitor.

35 Claims, 13 Drawing Sheets

(51) Int. Cl.
*A61B 34/30* (2016.01)
*A61B 90/00* (2016.01)

(58) Field of Classification Search
CPC ............ A61B 34/74; A61B 2034/2074; A61B 2034/305; A61B 2034/306; A61B 2034/741; A61B 2034/742; A61B 2034/743; A61B 2034/744; A61B 90/36; A61B 90/361; A61B 90/37; A61B 2090/3612; A61B 2090/364; A61B 2090/365; A61B 2090/368; A61B 2090/372; A61B 2090/502; A61B 50/10; A61B 50/13; A61B 2050/105; A61B 2017/00216; A61B 2017/00973
See application file for complete search history.

(56) References Cited

U.S. PATENT DOCUMENTS

| | | | | |
|---|---|---|---|---|
| 2020/0129250 | A1* | 4/2020 | Kapadia | A61B 34/25 |
| 2020/0138534 | A1* | 5/2020 | Garcia Kilroy | A61G 13/08 |
| 2020/0397524 | A1 | 12/2020 | Kapadia | |
| 2022/0175478 | A1* | 6/2022 | Kawabata | A61B 1/00045 |

* cited by examiner

PSAC - Stowed Isometric View

PSAC - Stowed Top View

MULTI-ARM ROBOTIC SURGICAL SYSTEM

TECHNICAL FIELD

The present disclosure generally relates to a multi-arm robotic surgical system for minimally invasive surgery, and more particularly, the disclosure relates to a five-arm configuration for robotic assisted surgery.

BACKGROUND

This section is intended to introduce the reader to various aspects of art that may be related to various aspects of the present disclosure, which are described below. This disclosure is believed to be helpful in providing the reader with background information to facilitate a better understanding of the various aspects of the present disclosure. Accordingly, it should be understood that these statements are to be read in this light, and not just as an admissions of prior art.

Robotically assisted surgical systems have been adopted worldwide to replace conventional surgical procedures to reduce number of extraneous tissue(s) that may be damaged during surgical or diagnostic procedures, thereby reducing patient recovery time, patient discomfort, prolonged hospital tenure, and particularly deleterious side effects. In robotically assisted surgeries, the surgeon typically operates a hand controller/master controller/surgeon input device at a surgeon console to seamlessly capture and transfer complex actions performed by the surgeon giving the perception that the surgeon is directly articulating surgical tools/surgical instruments to perform the surgery. The surgeon operating on the surgeon console may be located at a distance from a surgical site or may be located within an operating theatre where the patient is being operated.

The robotically assisted surgical systems comprises multiple robotic arms aiding in conducting robotic surgeries. The robotically assisted surgical system utilizes a sterile adapter/a sterile barrier to separate the non-sterile section of the robotic arm from a mandatory sterile surgical tool/surgical instrument attached to the robotic arm at an operating end. The sterile adaptor/sterile barrier may include a sterile plastic drape that envelops the robotic arm and the sterile adaptor/sterile barrier that operably engages with the sterile surgical tools/surgical instrument in a sterile field In robotic surgeries, a surgeon may need to hold any tissue, muscle, or organ, while performing the surgery. Also, if one robotic arm is used for holding a tissue/organ etc., then only two robotic arms are left to perform surgery. Especially in cardiothoracic surgeries, the surgeon may require holding a special surgical instrument like a clipper, stapler, or any suturing device. Thus, the main challenge with the existing robotically assisted surgical systems is that the maximum number of available robotic arms is limited to four including a camera arm. Another challenge is that, in the existing multi-arm robotic surgical systems, a particular hand controller movement by the surgeon may lead to collision of the arms during surgery.

In the light of aforementioned challenges, there is a need for multi-arm robotic surgical system which will solve the above-mentioned problems related to robotic assisted surgeries.

SUMMARY OF THE DISCLOSURE

Some or all of the above-mentioned problems related to providing training to the surgeons and OT staff are proposed to be addressed by certain embodiments of the present disclosure.

In one aspect, an embodiment of the present disclosure provides a multi-arm robotic surgical system comprising: a plurality of robotic arms arranged along an operating table; an endoscopic camera coupled to a robotic arm out of the plurality of robotic arms; a plurality of surgical instruments each detachably coupled to a robotic arm out of the remaining robotic arms; a surgeon console comprising: a master controller operably connected to the plurality of surgical instruments and the endoscopic camera, the master controller configured to provide control inputs to the plurality of surgical instruments and the endoscopic camera; a left-hand controller and a right-hand controller each coupled to the master controller, the left-hand controller and the right-hand controller are configured to receive input from a surgeon; a three-dimensional (3D) HD monitor configured to display a view of a surgical field in 3D; a two-dimensional (2D) touch screen monitor coupled to the master controller, the 2D touch screen monitor configured to be used as a graphical user interface to capture inputs from the surgeon; a head tracking camera operably connected to the master controller, the head tracking camera is secured to the 3D HD monitor; a pair of trackable 3D glasses configured to be tracked by the head tracking camera, the pair of trackable 3D glasses to be worn by the surgeon; a foot pedal controller connected to the master controller, the foot pedal controller configured to receive an input from the surgeon; a control panel configured to receive an input from the surgeon to perform functions for system ON/OFF, clear recoverable faults, and emergency stop; an electrosurgical unit interface connected to various surgical instruments out of the plurality of surgical instruments to provide an appropriate power signal to each of them; an image processor coupled to the endoscopic camera; the image processor configured to process a 3D image data received from the endoscopic camera; and a digital device configured to prepare an image data by using the processed 3D image data received from the image processor and superimposing it with a 2D overlay including a status of the plurality of surgical instruments; the digital device is further configured to transmit the prepared image data to the 3D HD monitor and a patient side staff 3D monitor.

Optionally, the plurality of surgical instruments includes general purpose surgical instruments like needle, forceps, grasper, clipper, and various cauterization surgical instruments like cutter, sealer, and coagulator etc.

Optionally, the 2D touch screen monitor is used to capture an input from the surgeon to turn on the master controller, toggle between real-time simulation, enable pre-operative functions, and to view a patient data.

Optionally, the foot pedal controller receives an input from the surgeon to perform functions for clutch, camera toggle, robotic arm toggle (left and right), cut cautery (left and right), coagulate cautery (left and right).

Optionally, the processed 3D image data from the image processor is recorded in a 3D HD image data recording system for future reference and recordkeeping.

Optionally, the surgeon console is outside the sterile field.

Optionally, each of the plurality of robotic arms connected to setup joints through a telescopic column, and further connected to a cart (608) through a vertical column, and a control dashboard, together form a patient side arm cart.

Optionally, each of the patient side arm cart is provided with parking locks.

Optionally, each patient side arm cart is placed partially within the sterile field.

Optionally, each patient side arm cart is provided with a battery backup.

Optionally, each patient side arm cart must be registered with the master controller before engaging the hand controllers.

Optionally, the control dashboard of each patient side arm cart includes a pair of drive switches, a 2D touch screen, a power ON/OFF button, an input button, a boom switch, a lock switch, a battery indicator, and a cart registration dial.

Optionally, the cart registration dial of each patient side arm cart is aligned perpendicular or parallel to the operating table.

Optionally, each robotic arm is placed within a sterile field.

Optionally, the robotic arm includes a plurality of active joints, a tool interface, and an actuator for a surgical instrument or endoscopic camera.

Optionally, the robotic arm further includes an instrument clutch button, primary arm clutch button, and a secondary arm clutch button.

Optionally, the plurality of robotic arms may be four or more robotic arms.

Optionally, the robotic surgical system is provided with an Un-interrupted power supply (UPS).

Optionally, the master controller manipulates the inputs to the plurality of surgical instruments for seamless control of the plurality of surgical instruments to mimic the surgeon's wrist and hand movements.

Optionally, the head tracking camera can be attached to the top of the 3D HD monitor.

Optionally, the head tracking camera helps in avoiding distracted system use and unintended motion.

Optionally, the hand controller manipulates the plurality of surgical instruments with four-degrees of freedom.

Optionally, the patient data includes diagnostic scan and patient details.

Optionally, the diagnostic scan comprises various medical scans, but not limited to MRI scan, CT scan, and the like, of one or more patients.

Optionally, the patient details comprise at least one of a name, age, sex, or medical history of one or more patients.

Optionally, the patient data can be fetched from at least one of a local database, or a server, or from a hospital picture archiving and communication system (PACS).

Optionally, the hand controller includes a hand gripper, a pinch grip button, a finger clutch button, and a hand sensor.

Optionally, the hand gripper can be grasped between thumb and index finger of left hand or right hand.

Optionally, the pinch grip button is configured to control the closure and opening of the jaw of a surgical instrument.

Optionally, the finger clutch button is configured to reorient the surgeon hand controller to a different space without compromising the position of the surgical instrument within the patient.

Optionally, the hand sensor will maintain the position of hand controller if left unattended by the surgeon.

Optionally, the hand controller has specific rotational and translational motions corresponding to the motions of the plurality of surgical instruments.

Optionally, the specific rotational motions of the hand controller (404, 406) include Roll, Pitch, and Yaw.

Optionally, the Roll rotational motion of the hand gripper controls the rotation of a surgical instrument along an axis 1.

Optionally, the Pitch rotational motion of the hand gripper controls the rotation of the surgical instrument along an axis 2.

Optionally, the Yaw rotational motion of the hand gripper controls the rotation of the surgical instrument along an axis 3.

Optionally, the height of the 3D HD monitor and hand controller can be adjusted by the surgeon.

Optionally, the position of the foot pedal can be adjusted up/down or in/out by the foot pedal controller.

Optionally, the robotic arm toggle (left and right) of the foot pedal controller includes a left robotic arm toggle pedal and a right robotic arm toggle pedal.

Optionally, the left robotic arm toggle pedal enables to swap between primary left and secondary left robotic arms and the right robotic arm toggle pedal enables to swap between primary right and secondary right robotic arms.

Optionally, the clutch of the foot pedal controller enables engaging/disengaging the hand controller for repositioning and engaging the plurality of surgical instruments.

Optionally, the translation motions corresponding to the motions of a surgical instrument translate the surgical instrument in and out of the surgical field or up/down and left/right translation of the surgical instrument along a remote centre of motion.

Optionally, the appropriate power signal provided to various cauterization surgical instruments out of the plurality of surgical instruments depends on the type of the instrument, like monopolar, bipolar, or harmonic.

Optionally, a preoperative 2D touch panel is provided for entering preoperative patient and surgical data by a patient side staff.

Other embodiments, systems, methods, apparatus aspects, and features of the invention will become apparent to those skilled in the art from the following detailed description, the accompanying drawings, and the appended claims. It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of the disclosure, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those skilled in the art will understand that the drawings are not to the scale. Wherever possible, like elements have been indicated by identical numbers.

Embodiments of the present disclosure will now be described, by way of example only, with reference to the following diagrams wherein:

FIG. 4(*b*) illustrates a control panel of the surgeon console in accordance with an embodiment of the disclosure;

FIG. 4(*c*) illustrates a surgeon hand controller of the surgeon console in accordance with an embodiment of the disclosure;

FIG. 4(*d*) illustrates various motions of the surgeon hand controller of the surgeon console in accordance with an embodiment of the disclosure;

FIG. 4(*e*) illustrates a foot pedal control of the surgeon console in accordance with an embodiment of the disclosure;

FIG. 6(*b*) illustrates various clutch buttons of the single arm of a patient side arm cart of the multi-arm teleoperated surgical system in accordance with an embodiment of the disclosure;

FIG. 6(*c*) illustrates a control dashboard provided on a patient side arm cart of the multi-arm teleoperated surgical system in accordance with an embodiment of the disclosure.

DETAILED DESCRIPTION OF THE DISCLOSURE

Figure 1:
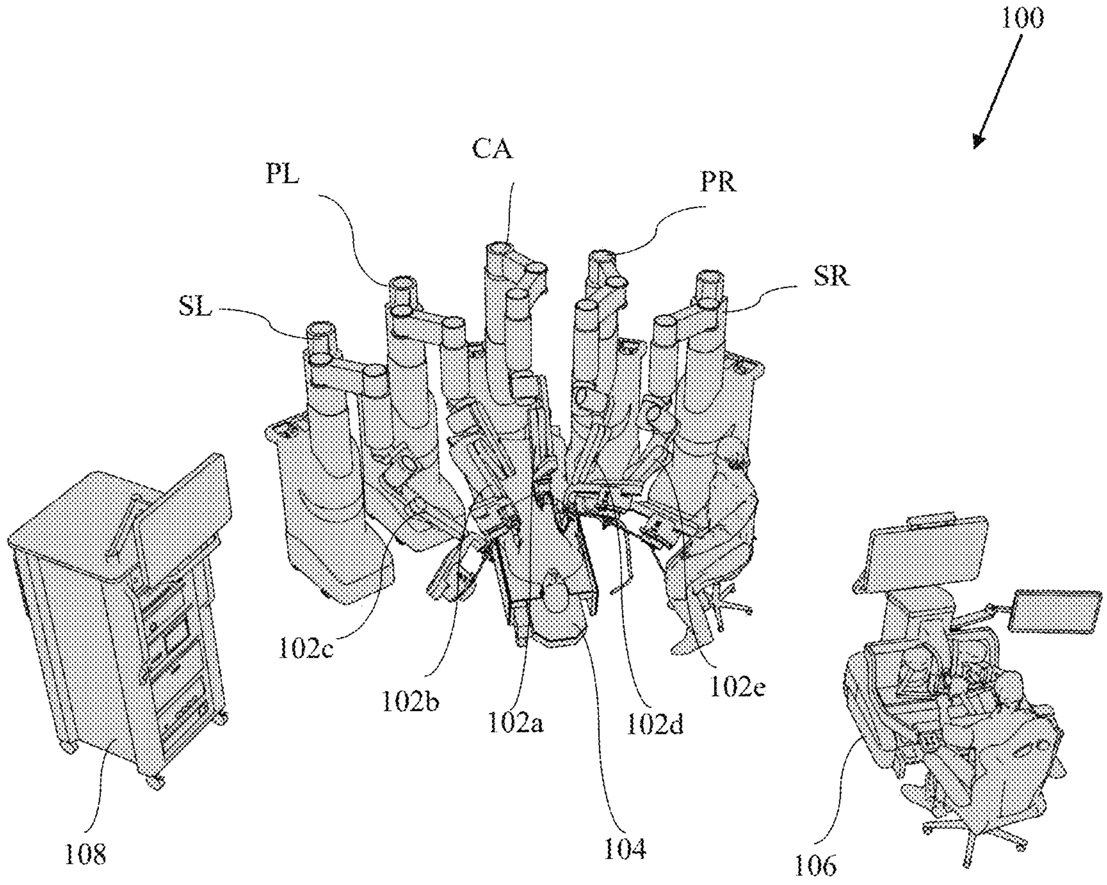
FIG. 1 illustrates an example implementation of a multi-arm teleoperated surgical system which can be used with one or more features in accordance with an embodiment of the disclosure.

For the purpose of promoting an understanding of the principles of the disclosure, reference will now be made to the embodiment illustrated in the drawings and specific language will be used to describe the same. It will nevertheless be understood that no limitation of the scope of the disclosure is thereby intended, such alterations and further modifications in the illustrated system, and such further applications of the principles of the disclosure as illustrated therein being contemplated as would normally occur to one skilled in the art to which the disclosure relates.

It will be understood by those skilled in the art that the foregoing general description and the following detailed description are exemplary and explanatory of the disclosure and are not intended to be restrictive thereof. Throughout the patent specification, a convention employed is that in the appended drawings, like numerals denote like components.

Reference throughout this specification to "an embodiment", "another embodiment", "an implementation", "another implementation" or similar language means that a particular feature, structure, or characteristic described in connection with the embodiment is included in at least one embodiment of the present disclosure. Thus, appearances of the phrase "in an embodiment", "in another embodiment", "in one implementation", "in another implementation", and similar language throughout this specification may, but do not necessarily, all refer to the same embodiment.

The terms "comprises", "comprising", or any other variations thereof, are intended to cover a non-exclusive inclusion, such that a process or method that comprises a list of steps does not include only those steps but may include other steps not expressly listed or inherent to such process or method. Similarly, one or more devices or sub-systems or elements or structures proceeded by "comprises . . . a" does not, without more constraints, preclude the existence of other devices or other sub-systems or other elements or other structures or additional devices or additional sub-systems or additional elements or additional structures.

Unless otherwise defined, all technical and scientific terms used herein have the same meaning as commonly understood by one of ordinary skill in the art to which this disclosure belongs. The device, system, and examples provided herein are illustrative only and not intended to be limiting.

The terms "a" and "an" herein do not denote a limitation of quantity, but rather denote the presence of at least one of the referenced items. Further, the term sterile barrier and sterile adapter denotes the same meaning and may be used interchangeably throughout the description.

Embodiments of the disclosure will be described below in detail with reference to the accompanying drawings.

FIG. 1 illustrates an example implementation of a multi arm teleoperated surgical system which can be used with one or more features in accordance with an embodiment of the disclosure. Specifically, FIG. 1 illustrates the multi arm teleoperated surgical system (100) having five robotic arms (102*a*), (102*b*), (102*c*), (102*d*), (102*e*), mounted on five robotic arm carts around an operating table (104). The five-robotic arms (102*a*), (102*b*), (102*c*), (102*d*), (102*e*), as depicted in FIG. 1 are for illustration purposes and the number of robotic arms may vary depending upon the type of surgery. The exemplary five robotic arms (102*a*), (102*b*), (102*c*), (102*d*), (102*e*), are arranged along the operating table (104) and may be arranged in different manner but not limited to the robotic arms (102*a*), (102*b*), (102*c*), (102*d*), (102*e*), arranged along the operating table (104). The robotic arms (102*a*), (102*b*), (102*c*), (102*d*), (102*e*), may be separately mounted on the five robotic arm carts or the robotic arms (102*a*), (102*b*), (102*c*), (102*d*), (102*e*), mechanically and/or operationally connected with each other or the robotic arms (102*a*), (102*b*), (102*c*), (102*d*), (102*e*), connected to a central body (not shown) such that the robotic arms (102*a*), (102*b*), (102*c*), (102*d*), (102*e*), branch out of a central body (not shown). Further, the multi arm teleoperated surgical system (100) may include a surgeon console (106), a vision cart (108), and a surgical instrument and accessory table.

Figure 2:
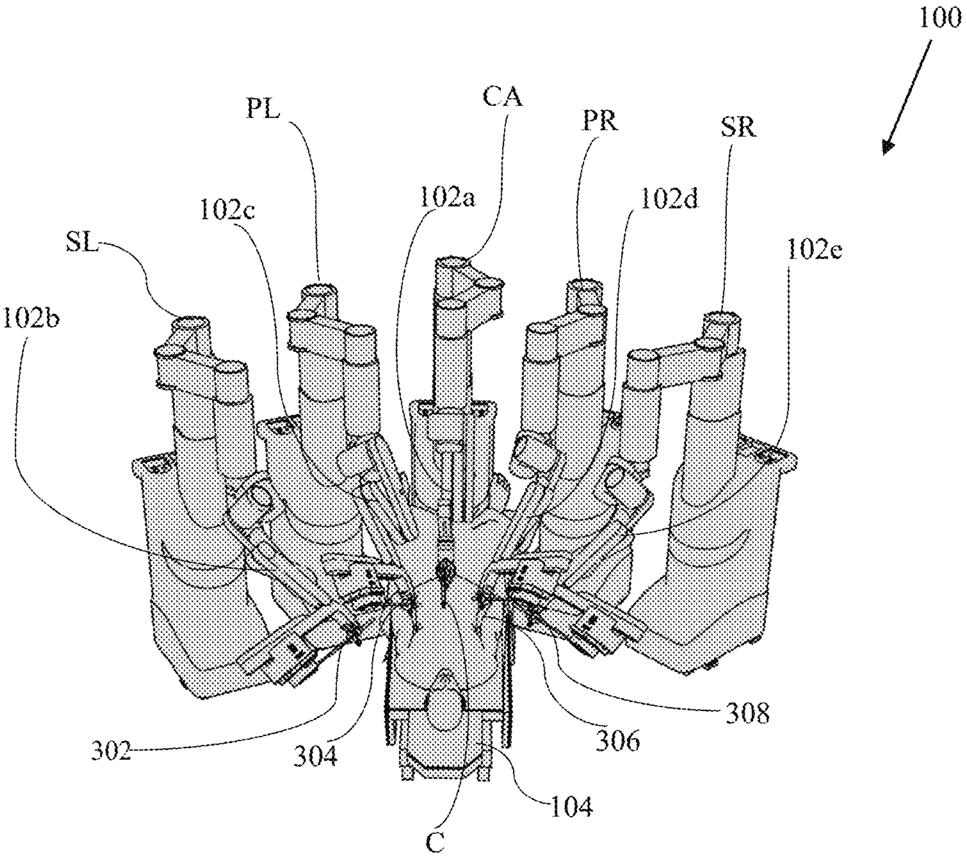
FIG. 2 illustrates a five-arm configuration of a patient side arm cart of the multi-arm teleoperated surgical system in accordance with an embodiment of the disclosure.

FIG. 2 illustrates a five-arm configuration of a patient side arm cart of the multi-arm teleoperated surgical system in accordance with an embodiment of the disclosure. According to an embodiment, the patient side arm carts are indicated as camera arm cart (CA), primary right robotic arm cart (PR), secondary right robotic arm cart (SR), primary left robotic arm cart (PL), and secondary left robotic arm cart (SL). The right and left position of the patient side arm cart carts (PSAC) is named with respect to the surgeon's endoscopic view and not the physical placement of the carts. This is only for identification purposes. An endoscopic camera (C) is coupled to the robotic arm (102*a*) attached to the camera arm cart (CA). In robotic surgeries, sometimes a surgeon needs to hold a tissue or organ, while performing suturing, clipping, cutting, sealing, and coagulating etc. Then, one robotic arm out of the remaining robotic arms (102*b*, 102*c*, 102*d*, 102*e*) can be utilized to hold the above-mentioned tissue or organ. Two of the other remaining robotic arms (102*b*, 102*c*, 102*d*, 102*e*) can be used for other surgical actions. Each of the plurality of surgical instruments (302, 304, 306, 308) is detachably coupled to a robotic arm out of the remaining robotic arms (102*b*, 102*c*, 102*d*, 102*e*), which in turn is connected to a patient side arm cart out of patient side arm carts (SL, PL, PR, SR).

Figure 3:
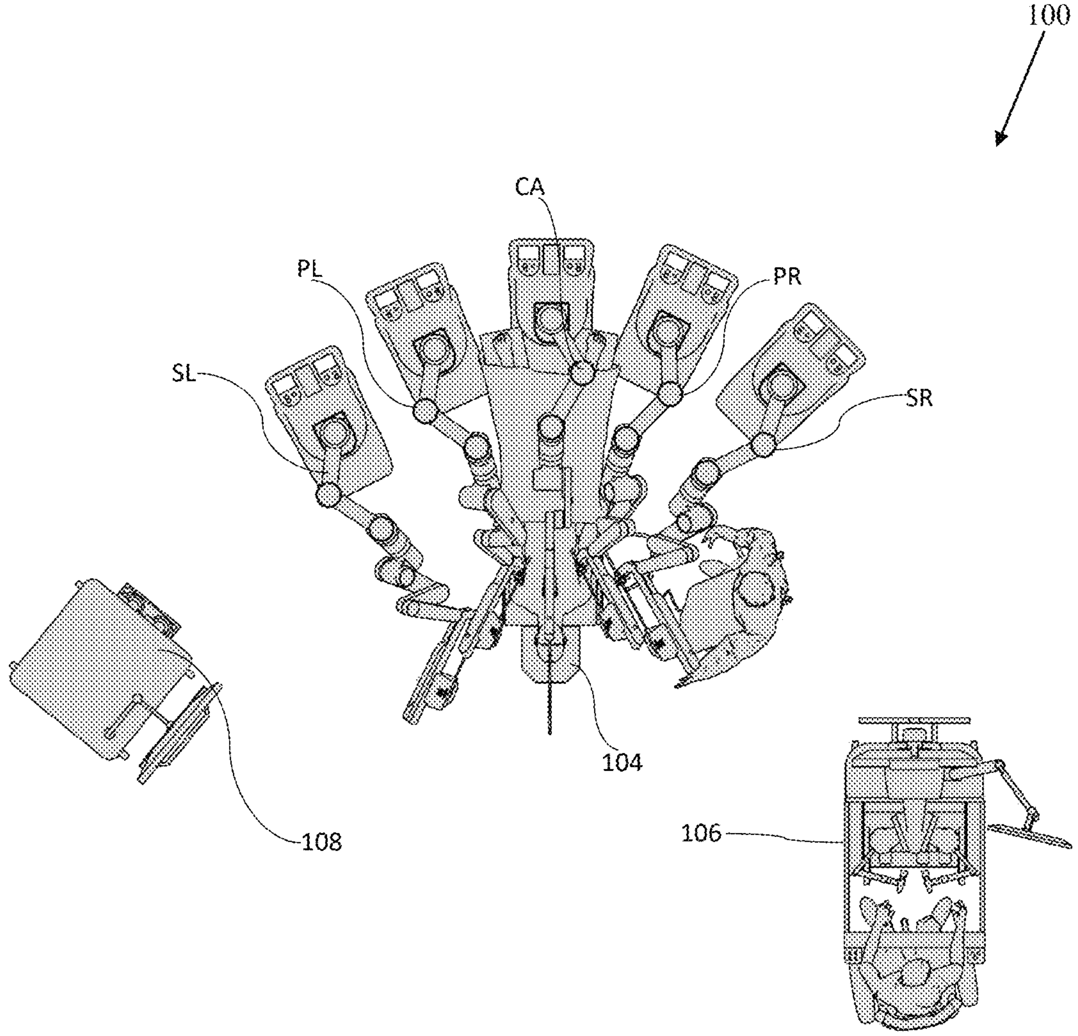
FIG. 3 illustrates another example implementation of a multi-arm teleoperated surgical system which can be used with one or more features in accordance with an embodiment of the disclosure.
Figure 4A:
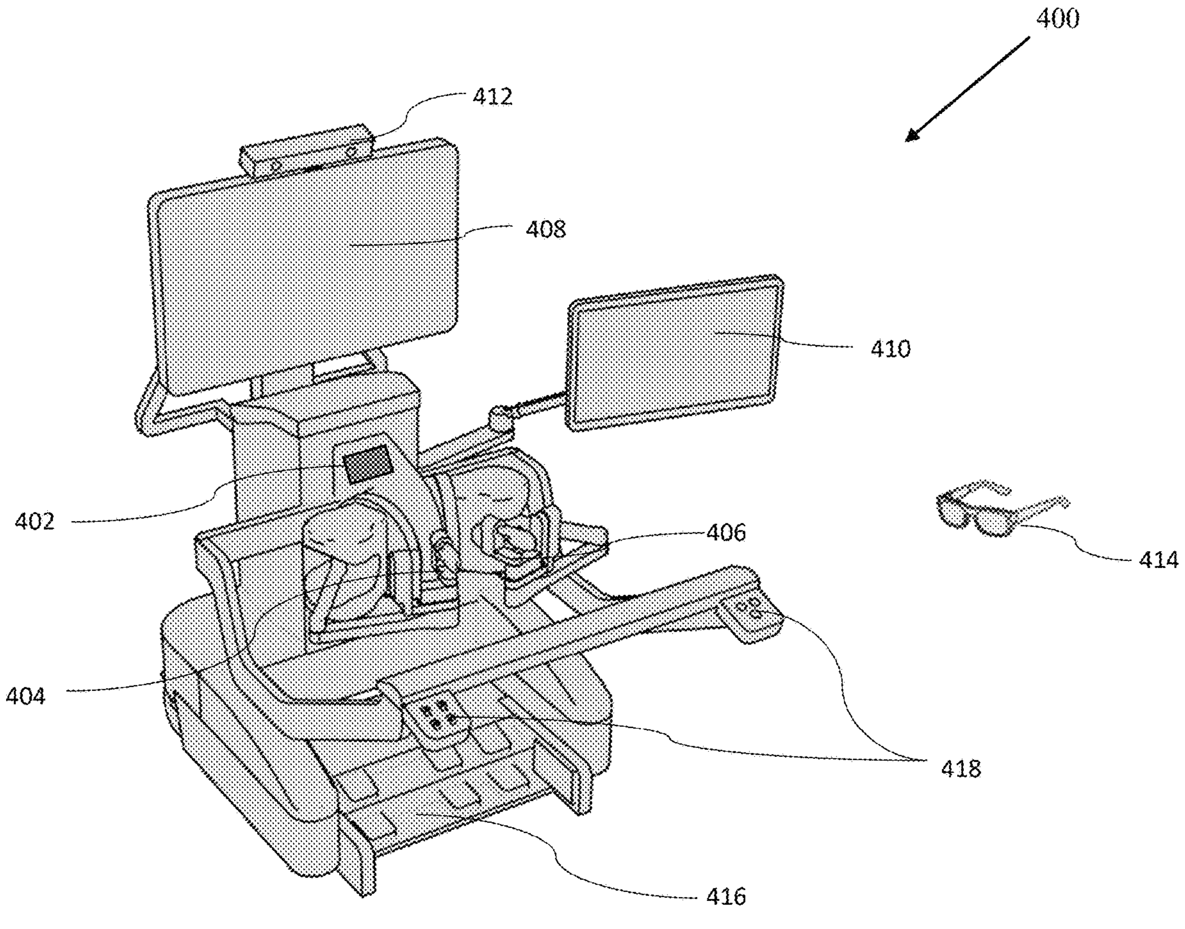
FIG. 4(*a*) illustrates a surgeon console in accordance with an embodiment of the disclosure.
Figure 4B:
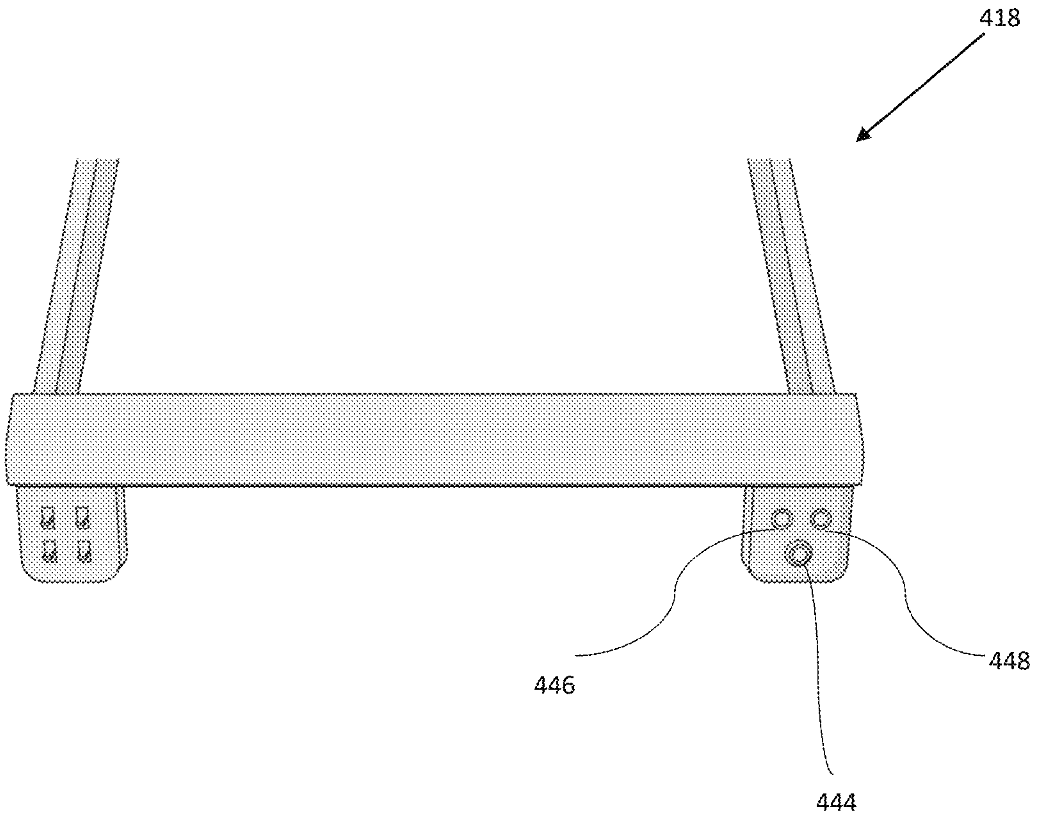
Figure 4C:
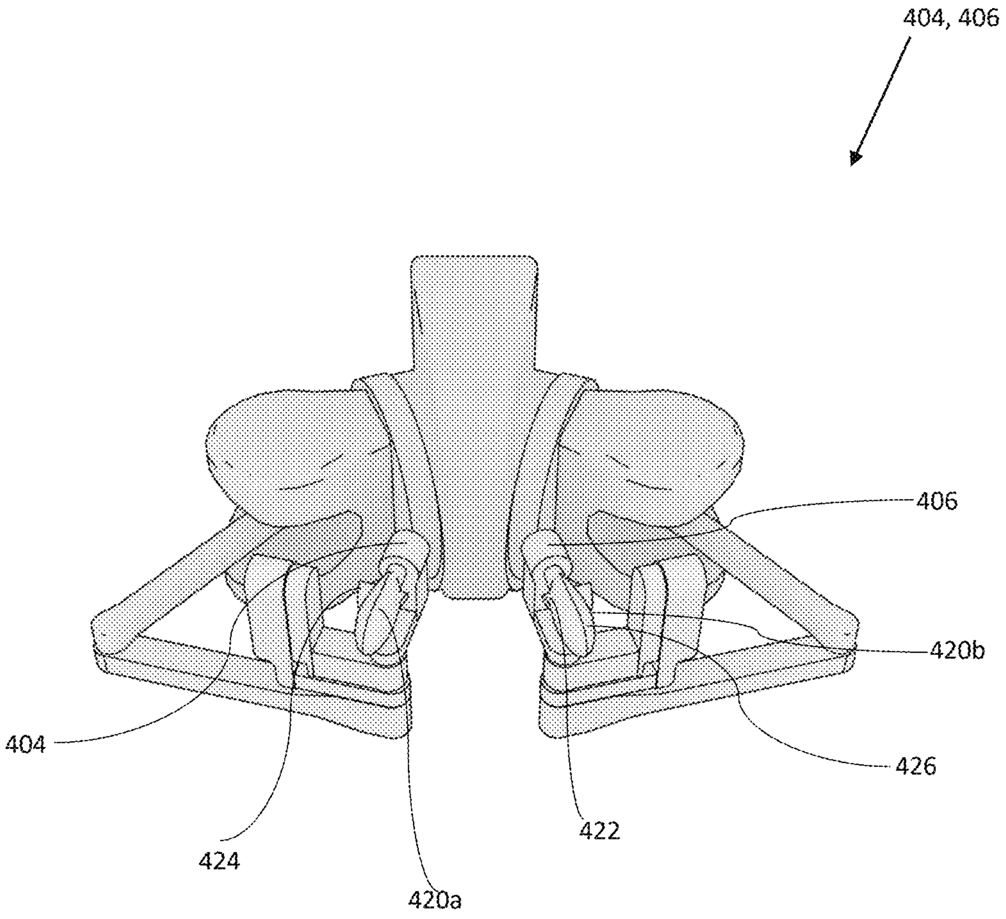
Figure 4D:
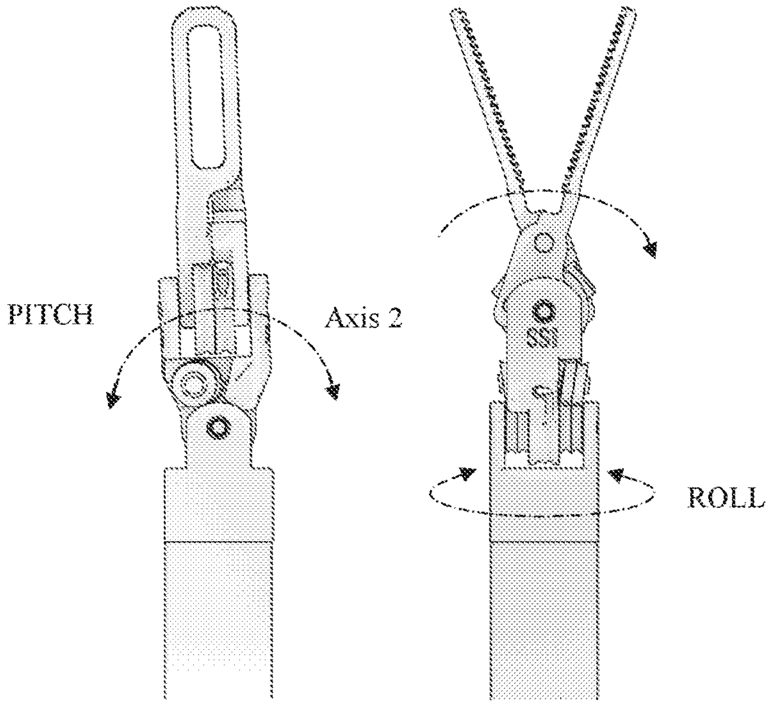
Figure 4E:
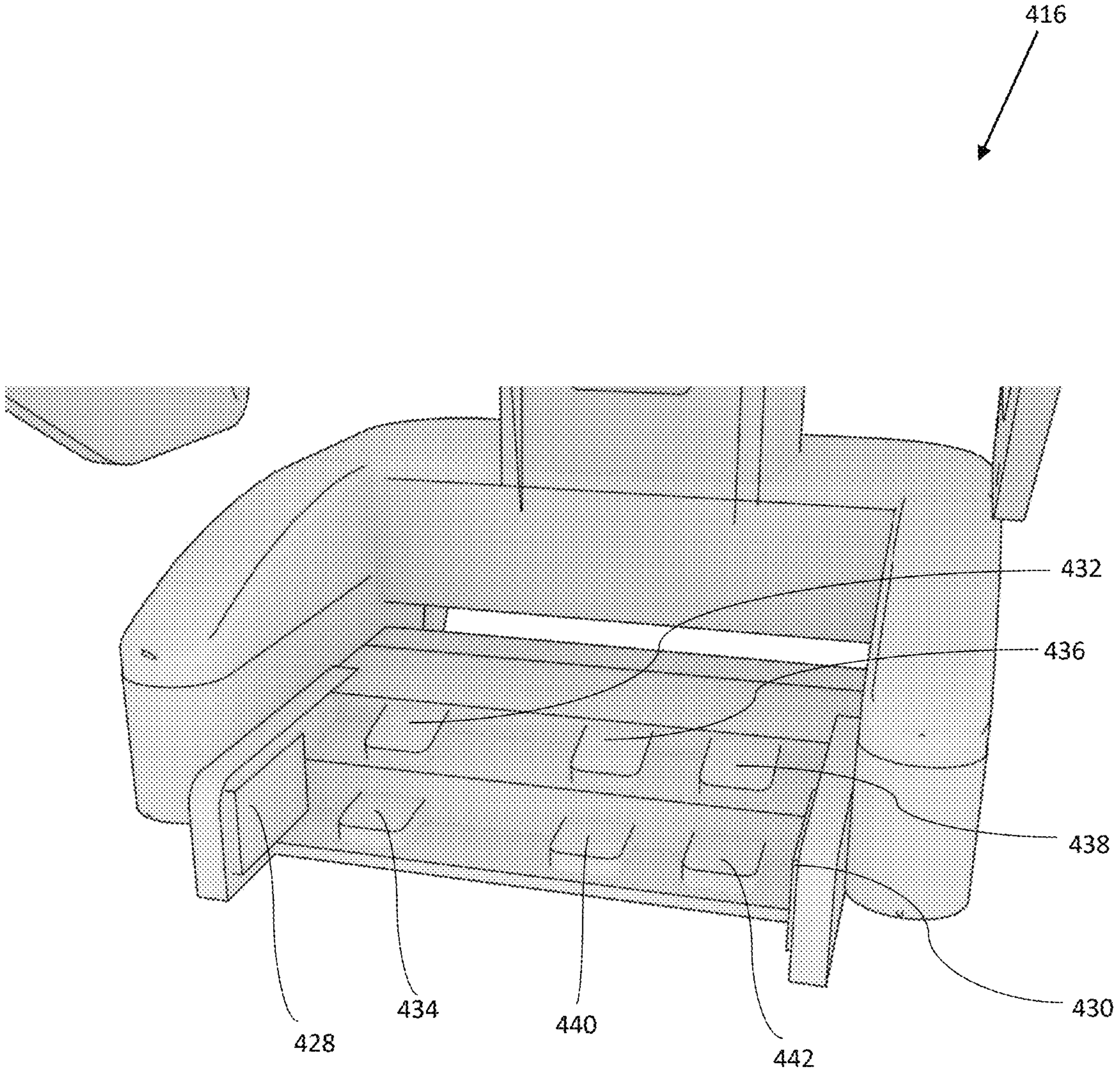

FIG. 3 illustrates exemplary implementation of a five-arm teleoperated surgical system which can be used with one or more features in accordance with an embodiment of the disclosure. Specifically, the secondary right robotic arm cart (SR) can be used in Cardiothoracic procedures.

FIG. 4(*a*) illustrates a surgeon console (400) in accordance with an embodiment of the disclosure. The surgeon console (400) comprises of a master controller (402) and acts as a surgeon command center (SCC). The surgeon console (400) is kept outside of the sterile field. According to an embodiment, the surgeon uses the surgeon console (400) to control the endoscopic camera and various surgical instruments via the patient side arm carts (SL, PL, CA, PR, SR). The surgeon console (400) is an open console with a 3D HD monitor (408) to display the endoscopic view of the surgical field in 3D. A left-hand controller (404) and a right-hand controller (406) are configured to receive input from a surgeon. The surgeon uses the hand controller (404, 406) to manipulate the endoscopic camera (C) and the surgical instruments (302, 304, 306, 308) with 4 degrees of motion. A surgeon wears a pair of trackable 3D glasses (414) to use with the surgeon console (400). The surgeon's pair of trackable 3D glasses (414) are tracked with a head tracking camera (412) which can be secured to the 3D HD monitor (408). Preferably, the head tracking camera (412) can be secured to the top of the 3D HD monitor (408). This is a safety feature to avoid distracted use of the multi-arm robotic surgical system (100) and unintended motions while the surgeon's attention is not focused on the 3D HD Monitor (408).

FIG. 4(*b*) illustrates a control panel (418) of the surgeon console (400) in accordance with an embodiment of the disclosure. The control panel (418) is provided, which houses buttons for performing functions for ON/OFF (444) of the multi-arm robotic surgical system (100), clear recoverable faults (446), and emergency stop (448). The button for ON/OFF (444) can be pressed to power the surgeon console (400) ON or OFF. The button clear recoverable faults (446) can be pressed to clear recoverable faults occurring at a system level. The emergency stop (448) can be pressed to shut down all system functions in case of an emergency.

FIG. 4(*c*) illustrates a surgeon hand controller (404, 406) of the surgeon console (400) in accordance with an embodiment of the disclosure. The hand controller (404, 406) includes a hand gripper (420*a*, 420*b*), a pinch grip button (422), a finger clutch button (424), and a hand sensor (426). The hand gripper (420*a*, 420*b*) can be grasped between the thumb and index finger of left hand or right hand. The pinch grip button (422) is configured to control the closure and opening of the jaw of a surgical instrument (302, 304, 306, 308) as illustrated in FIG. 4(*d*). The finger clutch button (424) is configured to reorient the surgeon's hand controller (404, 406) to a different space without compromising the position of the surgical instrument (302, 304, 306, 308) within the patient. The hand sensor (426) will maintain the position of hand controller (404, 406) if left unattended by the surgeon. The hand controller (404, 406) has specific rotational and translational motions corresponding to the motions of the plurality of surgical instruments (302, 304, 306, 308). The specific rotational motions of the hand controller (404, 406) include Roll, Pitch, and Yaw. The Roll rotational motion of the hand gripper (420*a*, 420*b*) controls the rotation of a surgical instrument (302, 304, 306, 308) along an axis 1 as shown in FIG. 4(*d*). The Pitch rotational motion of the hand gripper (420*a*, 420*b*) controls the rotation of the surgical instrument (302, 304, 306, 308) along an axis 2. The Yaw rotational motion of the hand gripper (420*a*, 420*b*) controls the rotation of the surgical instrument (302, 304, 306, 308) along an axis 3. The translation motions corresponding to the motions of a surgical instrument (302, 304, 306, 308) translate the surgical instrument (302, 304, 306, 308) in and out of the surgical field or up/down and left/right translation of the surgical instrument (302, 304, 306, 308) along a remote centre of motion (RCM). The plurality of surgical instruments (302, 304, 306, 308) includes general purpose surgical instruments like needle, forceps, grasper, clipper, and various cauterization surgical instruments like cutter, sealer, and coagulator etc. The hand controller provides the means for the surgeon to seamlessly control the instruments and endoscope inside the patient by replicating the surgeon's wrist and hand movements. The device is designed to allow natural range of motion and to provide ergonomic comfort, even during extended procedures.

The surgeon console (400) as shown in FIG. 4(*a*), further comprises of a foot pedal controller (416) to receive an input from the surgeon. Height of the surgeon console (400) can be adjusted by using various functions provided in the foot pedal controller (416) as illustrated in FIG. 4(*e*). The foot pedal controller (416) has buttons for various control actions. It houses the primary functions of clutch (432), camera toggle (434), robotic arm toggle (left and right) (428. 430), cut cautery (left and right) (436, 438), coagulate cautery (left and right) (440, 442). The clutch (432) can be pressed and held to disengage the surgeon hand controller (404, 406) for repositioning. The clutch (432) button is pressed and held before engaging the surgical instruments (302, 304, 306, 308), this will make sure that there are no unwanted motions on the robotic arms (102*b*, 102*c*, 102*d*, 102*e*) that may cause damage to the surgical instruments (302, 304, 306, 308) or the patient. The camera toggle (434) is pressed and held to maneuver the camera (C) in/out or up/down. The joystick on the endoscope can be manually used to articulate the tip of the endoscope for enhanced field of vision. There are provided robotic arm toggle left (428) and robotic arm toggle right (430) which can be pressed and held to swap between primary left (PL) and secondary left (SL) robotic arms and primary right (PR) and secondary right (SR) robotic arms in a four or five arm system. The cut cautery left (436) and cut cautery right (438) controls are provided to enable cutting function on the left robotic arm and right robotic arm respectively. The coagulate cautery left (440) and coagulate cautery right (442) controls are provided to enable the coagulation function on the left robotic arm and right robotic arm respectively.

The surgeon console (400) is further provided with a two-dimensional (2D) touch screen monitor (410) configured to be used as a graphical user interface to capture inputs from the surgeon, as illustrated in FIG. 4(*a*). The surgeon can use the 2D touch monitor (410) to turn on the multi-arm robotic surgical system (100), toggle between real-time simulation, enable pre-operative functions and to view patient data through the hospital picture archiving and communication system (PACS).

Figure 5:
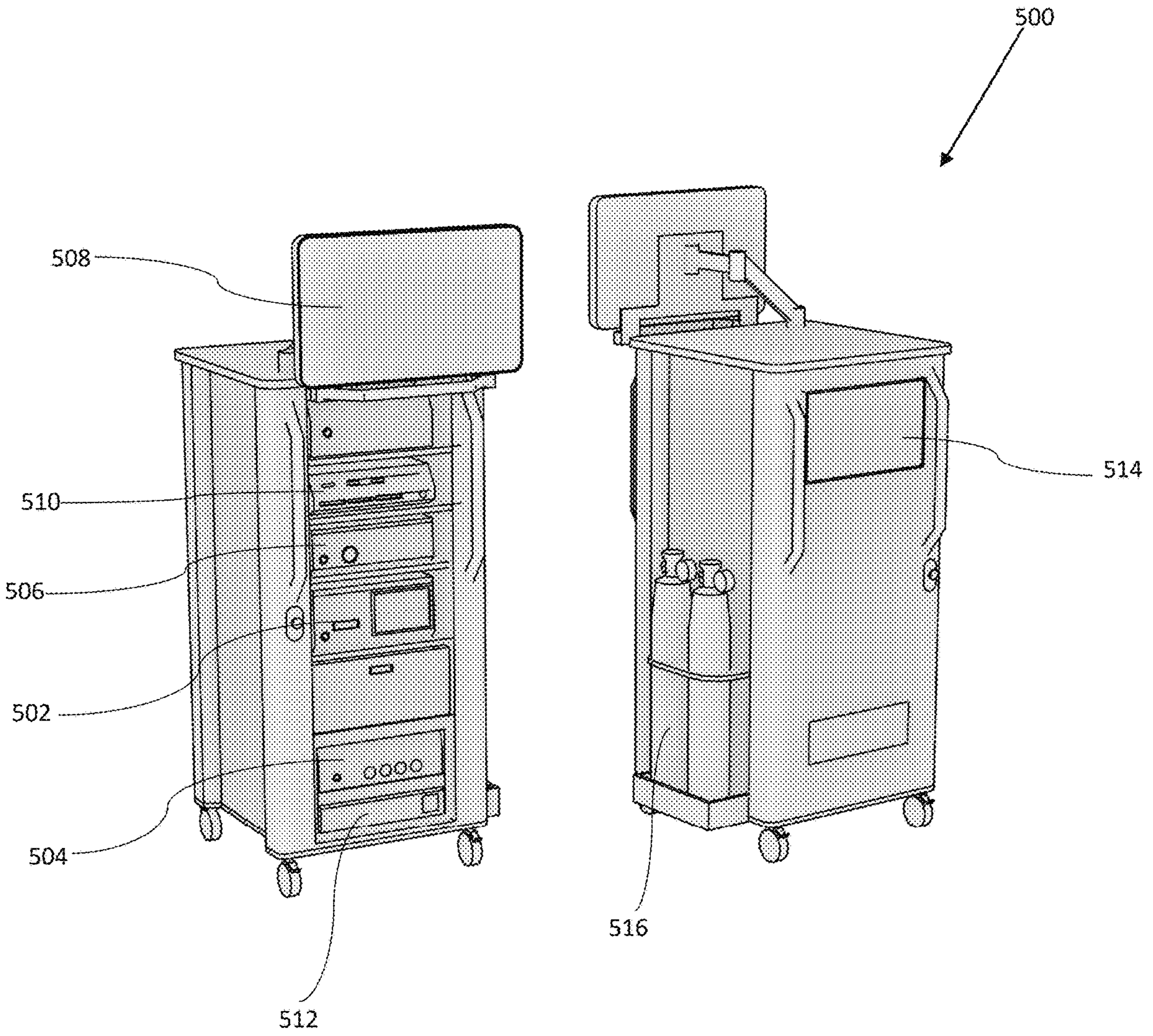
FIG. 5 illustrates a vison cart in accordance with an embodiment of the disclosure.

FIG. 5 illustrates a vison cart (500) in accordance with an embodiment of the disclosure. The vision cart (500) houses many of the electronic components and controls of the robotic surgical system such as an electrosurgical unit interface (502), an image processor (504), a digital device (506), patient side staff 3D monitor (508), a 3D HD image data recording system (510), an Un-interrupted power supply (UPS) (512), and a pre-operative 2D touch panel (514). The electrosurgical unit interface (502) is connected to various cauterization surgical instruments out of the plurality of surgical instruments (302, 304, 306, 308) to provide an appropriate power signal to each of them. The appropriate power signal provided to various cauterization surgical instruments out of the plurality of surgical instruments (302, 304, 306, 308) depends on the type of the instrument (302, 304, 306, 308), like monopolar, bipolar, or harmonic.

The image processor (504) is coupled to the endoscopic camera (C) connected to the robotic arm (102*a*). The image processor (504) is configured to process a 3D image data received from the endoscopic camera (C). The processed 3D image data from the image processor (504) is recorded in the 3D HD image data recording system (510) for future reference and recordkeeping. The digital device (506) is configured to prepare an image data by using the processed 3D image data received from the image processor (504) and superimposing it with a 2D overlay including a status of the plurality of surgical instruments (302, 304, 306, 308). The digital device (506) is further configured to transmit the prepared image data to the 3D HD monitor (408) and a patient side staff 3D monitor (508). The multi-arm robotic surgical system (100) is provided with an Un-interrupted power supply (UPS) (512). The pre-operative 2D touch panel (514) is provided for entering preoperative patient and surgical data by a patient side staff. Additionally, space provision for tools, cables, and $CO_2$ cylinder bay (516) is provided in the vision cart (500).

Figure 6A:
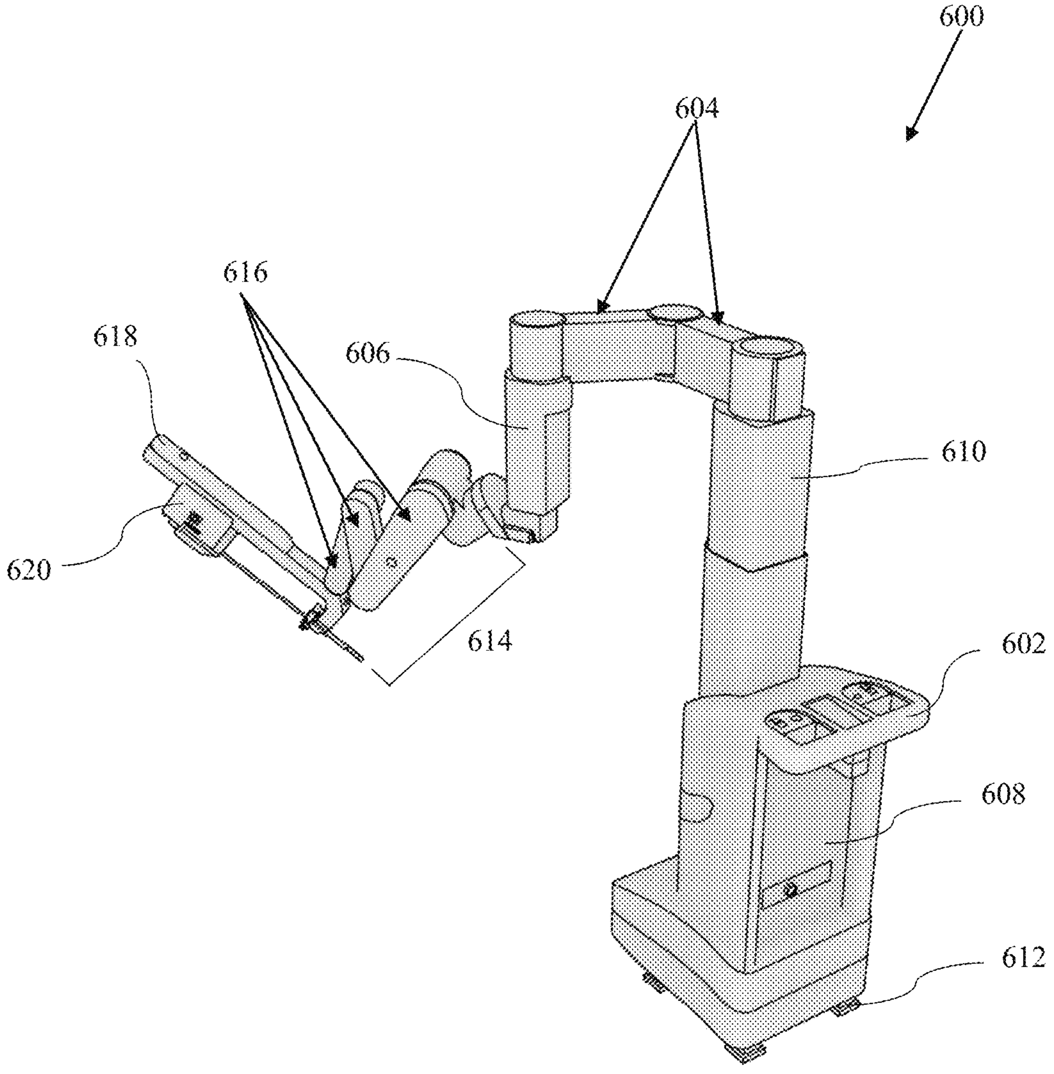
FIG. 6(*a*) illustrates a single arm of a patient side arm cart of the multi-arm teleoperated surgical system in accordance with an embodiment of the disclosure.
Figure 6B:
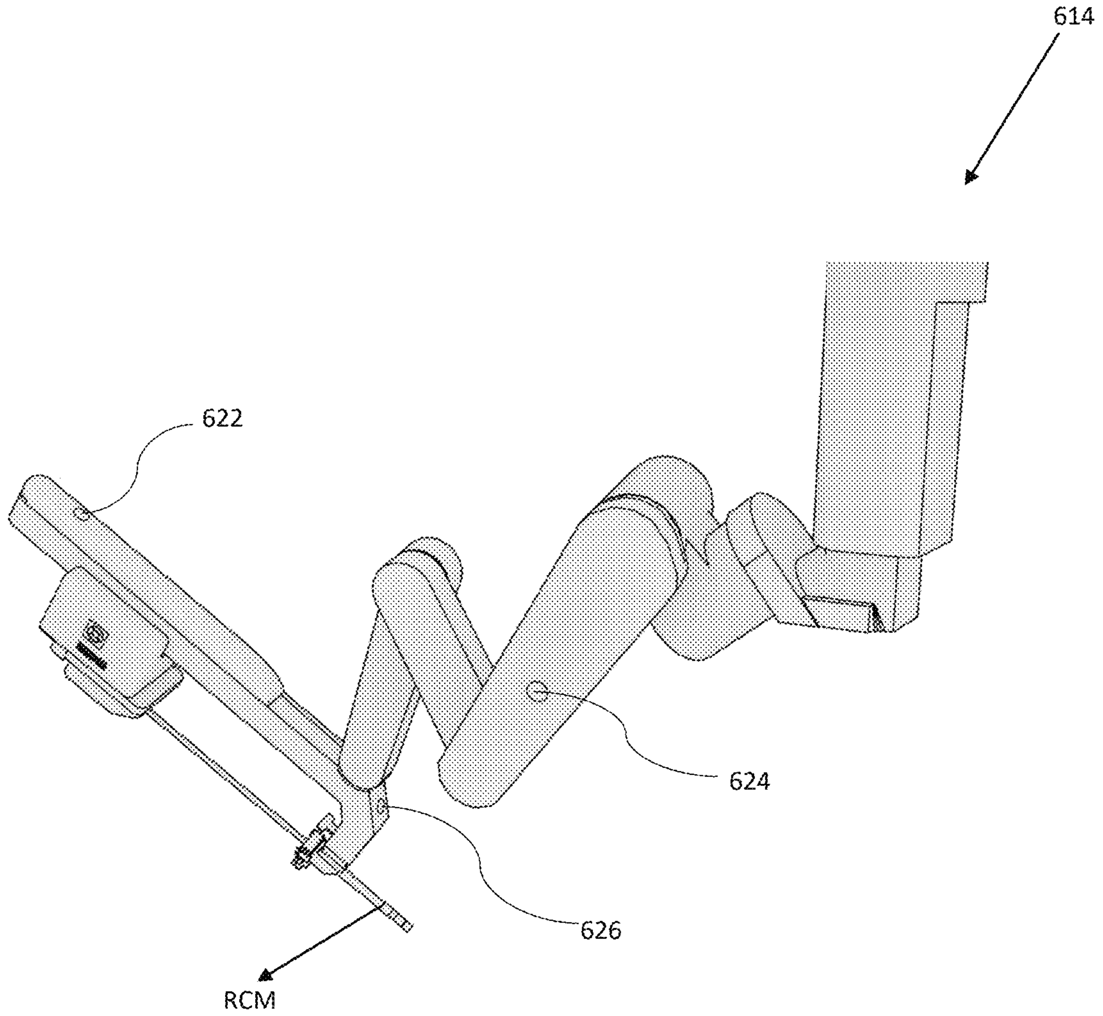
Figure 6C:
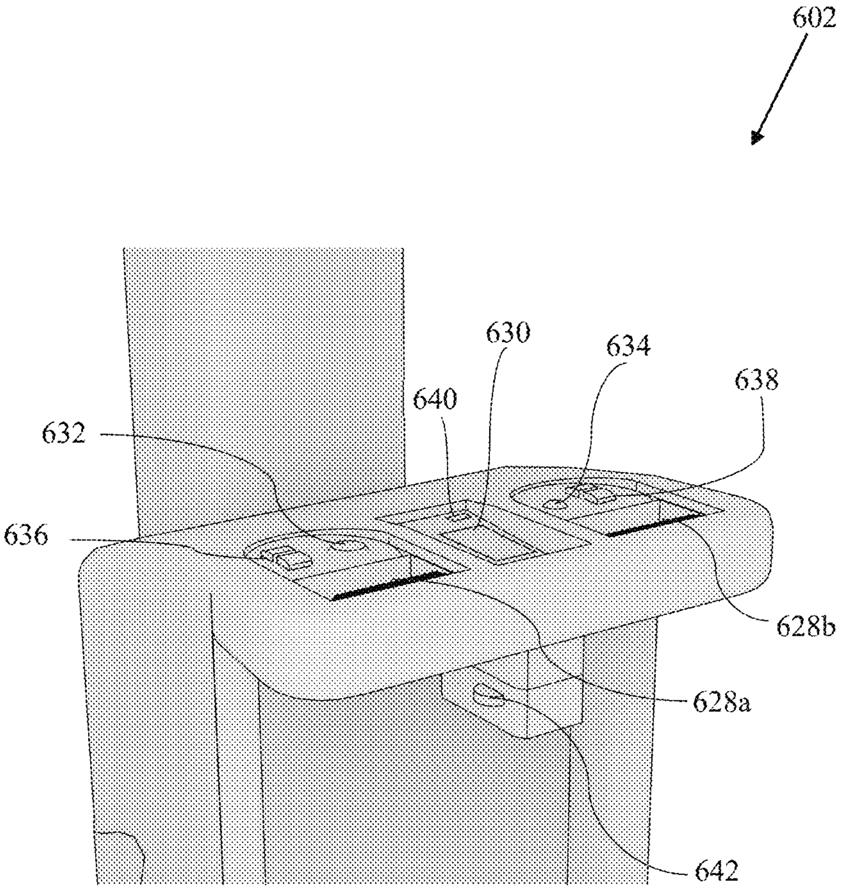

FIG. 6 (*a*) illustrates a single arm of a patient side arm cart (600) of the multi-arm teleoperated surgical system in accordance with an embodiment of the disclosure. Each of the plurality of robotic arms (614) (reference numeral (614) depicts robotic arm components attached distally to a telescopic column (606)) is connected to setup joints (604) through a telescopic column (606), and further connected to a cart (608) through a vertical column (610), and a control dashboard (602), which together form a patient side arm cart (600) (reference numeral (600) depicts a single patient side arm cart). Each patient side arm cart 600 is provided with a battery backup and parking locks (612). Each patient side arm cart (600) is placed partially within the sterile field. Each patient side arm cart (600) must be registered with the master controller (402) before engaging the hand controllers (404, 406). The robotic arm (614) includes a plurality of active joints (616), a tool interface (618), and an actuator (620) for a surgical instrument (302, 304, 306, 308) or an endoscopic camera (C). Further, to avoid collision between robotic arms (614) in relation to any particular hand controller movement by a surgeon, the patient side arm carts (600) can be used in inverted robotic arm configuration, as shown in FIG. 2.

FIG. 6 (*b*) illustrates various clutch buttons of the single arm of a patient side arm cart of the multi-arm teleoperated surgical system (100) in accordance with an embodiment of the disclosure. Each of the robotic arm (614) further includes an instrument clutch button (622), primary arm clutch button (624), and a secondary arm clutch button (626). The instrument clutch button (622) is pressed and held to open or close the active joints of the robotic arm while maintaining the pivot point of the Instrument/endoscope at the Remote Center of Motion (RCM). The primary arm clutch button (624) is pressed and held to release the brakes on the Setup Joints and the Telescopic Column to move the robotic arm joint setup in free space and to raise or lower the Telescopic Column as required. The secondary arm clutch button (626) is pressed and held to release the brakes on the Setup Joints and the Telescopic Column to move the robotic arm joint setup in free space and to raise or lower the Telescopic Column as required. This button is ideally used during docking to bring the robotic arm closer to the patient for cannula mounting.

FIG. 6 (*c*) illustrates a control dashboard (602) provided on a patient side arm cart of the multi-arm teleoperated surgical system (100) in accordance with an embodiment of the disclosure. The control dashboard (602) of each patient side arm cart (600) includes a pair of drive switches (628*a*, 628*b*), a 2D touch screen (630), a power ON/OFF button (632), an input button (634), a boom switch (636), a lock switch (638), a battery indicator (640), and a cart registration dial (642). The pair of drive switches (628*a*, 628*b*) are pressed and held to enable drive mode. While holding the pair of drive switches (628*a*, 628*b*), the handles are gently pushed or pulled to move each patient side arm cart (600) forward or backward respectively.

As illustrated in FIG. 6 (*c*), the 2D touch screen (630) can be used as a quick reference guide for driving each patient side arm cart (600). The power ON/OFF button (632) of each patient side arm cart (600) is pressed to turn it ON/OFF. The input button (634) is pressed after aligning the Cart registration dials (642) of all the carts either parallel or perpendicular to the patient bed. This will enable registering each patient side arm cart (600) in the world space for cart registration and simulation functions. The boom switch (636) is pressed and held up/down to raise/lower the vertical column to the desired height. Height markers are provided on the vertical column, which indicate the maximum attainable height of the vertical column, ideal height of the vertical column for draping, and minimum height at which the vertical column needs to be stowed at. The lock switch (638) is pressed and held up/down to unlock the parking locks for driving and to lock the parking locks for docking. The battery indicator (640) indicates the level of charge left in the battery provided with each patient side arm cart (600) The green color indicates a charge of 100% to 60%, blue color indicates a charge of 60% to 20%, and the red color indicates a charge below 20%. The cart registration dial (642) function is completed before engaging the surgeon hand Controller (404, 406). Failure to do so will cause damage to the surgical instruments (302, 304, 306, 308). The Cart Registration Dials of all the patient side arm cart (600) are aligned either (a) perpendicularly or (b) parallelly in reference to the operating table (104).

Figure 7:
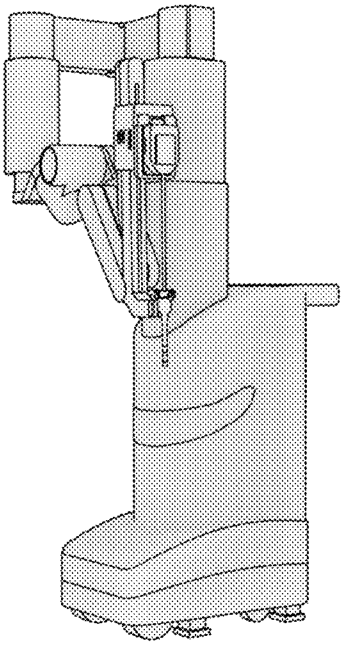
FIG. 7 illustrates an isometric view and top view respectively of a single arm of a patient side arm cart of the multi-arm teleoperated surgical system in accordance with an embodiment of the disclosure.
Figure 7:
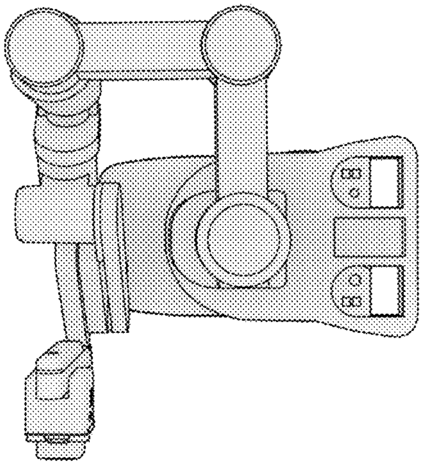

FIG. 7 illustrates an isometric view and top view respectively of a single arm of a patient side arm cart of the multi-arm teleoperated surgical system in accordance with an embodiment of the disclosure.

The foregoing description of exemplary embodiments of the present disclosure has been presented for purposes of illustration and description. They are not intended to be exhaustive or to limit the disclosure to the precise forms disclosed, and obviously many modifications and variations are possible in light of the above teaching. The exemplary embodiment was chosen and described in order to best explain the principles of the disclosure and its practical application, to thereby enable others skilled in the art to best utilize the disclosure and various embodiments with various modifications as are suited to the particular use contemplated. It is understood that various omissions, substitutions of equivalents are contemplated as circumstance may suggest or render expedient but is intended to cover the application or implementation without departing from the spirit or scope of the claims of the present disclosure.

Benefits, other advantages, and solutions to problems have been described above with regard to specific embodiments. However, the benefits, advantages, solutions to problems, and any component(s) that may cause any benefit, advantage, or solution to occur or become more pronounced are not to be construed as a critical, required, or essential feature or component of any or all the claims.

While specific language has been used to describe the disclosure, any limitations arising on account of the same are not intended. As would be apparent to a person in the art, various working modifications may be made to the apparatus in order to implement the inventive concept as taught herein.

List of reference numerals:

| Sr. No. | Component | Reference Numeral(s) |
|---|---|---|
| 1 | Robotic arms | 102a, 102b, 102c, 102d, 102e |
| 2 | Operating table | 104 |
| 3 | Endoscopic camera | C |
| 4 | Surgical instruments | 302, 304, 306, 308 |
| 5 | Surgeon console | 400 |
| 6 | Master controller | 402 |
| 7 | Three-dimensional (3D) HD monitor | 408 |
| 8 | Two-dimensional (2D) touch screen monitor | 410 |
| 9 | Head tracking camera | 412 |
| 10 | Trackable 3D glasses | 414 |
| 11 | Foot pedal controller | 416 |
| 12 | Control panel | 418 |
| 13 | System ON/OFF | 444 |
| 14 | Clear recoverable faults | 446 |
| 15 | Emergency stop | 448 |
| 16 | Electrosurgical unit interface | 502 |
| 17 | Image processor | 504 |
| 18 | Digital device | 506 |
| 19 | Patient side staff 3D monitor | 508 |
| 20 | Clutch | 432 |
| 21 | Camera toggle | 434 |
| 22 | Robotic arm toggle (left and right) | 428, 430 |
| 23 | Cut cautery (left and right) | 436, 438 |
| 24 | Coagulate cautery | 440, 442 |
| 25 | 3D HD image data recording system | 510 |
| 26 | Multi-arm robotic surgical system | 100 |
| 27 | Setup joints | 604 |
| 28 | Telescopic column | 606 |
| 29 | Cart | 608 |
| 30 | Vertical column | 610 |
| 31 | Control dashboard | 602 |
| 32 | Patient side arm cart | SL, PL, CA, PR, SR |
| 33 | Parking locks | 612 |
| 34 | Hand controller | 404, 406 |
| 35 | Pair of drive switches | 628a, 628b |
| 36 | 2D touch screen | 630 |
| 37 | Power ON/OFF button | 632 |
| 38 | Input button | 634 |
| 39 | Boom switch | 636 |
| 40 | Lock switch | 638 |
| 41 | Battery indicator | 640 |
| 42 | Cart registration dial | 642 |
| 43 | Active joints | 616 |
| 44 | Tool interface | 618 |
| 45 | Actuator | 620 |
| 46 | Instrument clutch button | 622 |
| 47 | Primary arm clutch button | 624 |
| 48 | Secondary arm clutch button | 626 |
| 49 | Hand gripper | 420a, 420b |
| 50 | Pinch grip button | 422 |
| 51 | Finger clutch button | 424 |
| 52 | Hand sensor | 426 |
| 53 | Left robotic arm toggle pedal | 428 |
| 54 | Right robotic arm toggle pedal | 430 |
| 55 | Pre-operative 2D touch panel | 514 |

We claim:

1. A multi-arm robotic surgical system comprising:

a plurality of robotic arms arranged along an operating table;

an endoscopic camera (C) coupled to a robotic arm out of the plurality of robotic arms;

a plurality of surgical instruments each detachably coupled to a robotic arm out of the remaining robotic arms;

a surgeon console comprising:

a master controller operably connected to the plurality of surgical instruments and the endoscopic camera (C), the master controller configured to provide control inputs to the plurality of surgical instruments and the endoscopic camera (C);

a left-hand controller and a right-hand controller each coupled to the master controller, the left-hand controller and the right-hand controller are configured to receive input from a surgeon;

a three-dimensional (3D) HD monitor configured to display a view of a surgical field in 3D;

a two-dimensional (2D) touch screen monitor coupled to the master controller, the 2D touch screen monitor configured to be used as a graphical user interface to capture inputs from the surgeon;

a head tracking camera operably connected to the master controller, the head tracking camera is secured to the 3D HD monitor;

a pair of trackable 3D glasses configured to be tracked by the head tracking camera, the pair of trackable 3D glasses to be worn by the surgeon;

a foot pedal controller connected to the master controller, the foot pedal controller configured to receive an input from the surgeon, wherein the robotic arm toggle (left and right) of the foot pedal controller includes a left robotic arm toggle pedal and a right robotic arm toggle pedal; and wherein the left robotic arm toggle pedal enables to swap between primary left and secondary left robotic arms and the right robotic arm toggle pedal enables to swap between primary right and secondary right robotic arms;

a control panel configured to receive an input from the surgeon to perform functions for system ON/OFF; clear recoverable faults; and emergency stop;

an electrosurgical unit interface connected to various surgical instruments out of the plurality of surgical instruments to provide an appropriate power signal to each of them;

an image processor coupled to the endoscopic camera (C); the image processor configured to process a 3D image data received from the endoscopic camera (C); and a digital device configured to prepare an image data by using the processed 3D image data received from the image processor and superimposing it with a 2D overlay including a status of the plurality of surgical instruments; the digital device is further configured to transmit the prepared image data to the 3D HD monitor and a patient side staff 3D monitor;

wherein each of the plurality of robotic arms connected to a setup joints through a telescopic column; and further connected to a cart through a vertical column (610); and a control dashboard; which together form a patient side arm cart (SL; PL; CA; PR; SR);

wherein each patient side arm cart (SL; PL; CA; PR; SR) is provided with parking locks;

wherein each patient side arm cart (SL; PL; CA; PR; SR) is placed partially within a sterile field;

wherein each patient side arm cart (SL; PL; CA; PR; SR) is provided with a battery backup; and wherein each patient side arm cart (SL; PL; CA; PR; SR) must be registered with the master controller before engaging the left-hand controller and the right-hand controller.

2. The multi-arm robotic surgical system as claimed in claim 1, wherein the plurality of surgical instruments includes needle, forceps, grasper, clipper, cutter, sealer, and coagulator.

3. The multi-arm robotic surgical system as claimed in claim 1, wherein the 2D touch screen monitor is used to capture an input from the surgeon to turn on the master controller, toggle between real-time simulation, enable pre-operative functions, and to view a patient data.

4. The multi-arm robotic surgical system as claimed in claim 3, wherein the patient data includes diagnostic scan and patient details.

5. The multi-arm robotic surgical system as claimed in claim 4, wherein the diagnostic scan comprises MRI scan, CT scan of one or more patients.

6. The multi-arm robotic surgical system as claimed in claim 4, wherein the patient details comprise at least one of a name, age, sex, or medical history of one or more patients.

7. The multi-arm robotic surgical system as claimed in claim 3, wherein the patient data is configured to be fetched from at least one of a local database, or a server, or from a hospital picture archiving and communication system (PACS).

8. The multi-arm robotic surgical system as claimed in claim 1, wherein the foot pedal controller receives an input from the surgeon to perform functions for a clutch, a camera toggle, a robotic arm toggle (left and right), a cut cautery (left and right), a coagulate cautery (left and right).

9. The multi-arm robotic surgical system as claimed in claim 1, wherein the processed 3D image data from the image processor is recorded in a 3D HD image data recording system for future reference and recordkeeping.

10. The multi-arm robotic surgical system as claimed in claim 1, wherein the surgeon console is outside the sterile field.

11. The multi-arm robotic surgical system as claimed in claim 1, wherein each robotic arm is placed within sterile field.

12. The multi-arm robotic surgical system as claimed in claim 1, wherein the plurality of robotic arm includes a plurality of active joints, a tool interface, and an actuator.

13. The multi-arm robotic surgical system as claimed in claim 1, wherein the plurality of robotic arm includes an instrument clutch button, a primary arm clutch button, and a secondary arm clutch button.

14. The multi-arm robotic surgical system as claimed in claim 1, wherein the plurality of robotic arms comprise four or more robotic arms, right) of the foot pedal controller includes a left robotic arm toggle pedal and a right robotic arm toggle pedal; and wherein the left robotic arm toggle pedal enables to swap between primary left and secondary left robotic arms and the right robotic arm toggle pedal enables to swap between primary right and secondary right robotic arms;

a control panel configured to receive an input from the surgeon to perform functions for system ON/OFF, clear recoverable faults, and emergency stop;

an electrosurgical unit interface connected to various surgical instruments out of the plurality of surgical instruments to provide an appropriate power signal to each of them;

an image processor coupled to the endoscopic camera (C); the image processor configured to process a 3D image data received from the endoscopic camera (C); and a digital device configured to prepare an image data by using the processed 3D image data received from the image processor and superimposing it with a 2D overlay including a status of the plurality of surgical instruments; the digital device is further configured to transmit the prepared image data to the 3D HD monitor and a patient side staff 3D monitor;

wherein each of the plurality of robotic arms connected to a setup joints through a telescopic column, and further connected to a cart through a vertical column (610), and a control dashboard, which together form a patient side arm cart (SL, PL, CA, PR, SR);

wherein each patient side arm cart (SL, PL, CA, PR, SR) is provided with parking locks;

wherein each patient side arm cart (SL, PL, CA, PR, SR) is placed partially within a sterile field;

wherein each patient side arm cart (SL, PL, CA, PR, SR) is provided with a battery backup; and wherein each patient side arm cart (SL, PL, CA, PR, SR) must be registered with the master controller before engaging the left-hand controller and the right-hand controller.

15. The multi-arm robotic surgical system as claimed in claim 1, wherein the robotic surgical system is provided with an Un-interrupted power supply (UPS).

16. The multi-arm robotic surgical system as claimed in claim 1, wherein the master controller manipulates the inputs to the plurality of surgical instruments for seamless control of the plurality of surgical instruments to mimic the surgeon's wrist and hand movements.

17. The multi-arm robotic surgical system as claimed in claim 1, wherein the head tracking camera attached to the top of the 3D HD monitor.

18. The multi-arm robotic surgical system as claimed in claim 1, wherein the head tracking camera helps in avoiding distracted multi-arm robotic surgical system use and unintended motion.

19. The multi-arm robotic surgical system as claimed in claim 1, wherein the left-hand controller and the right-hand controller manipulates the plurality of surgical instruments with four-degrees of freedom.

20. The multi-arm robotic surgical system as claimed in claim 1, wherein the left-hand controller and the right-hand controller includes a hand gripper, a pinch grip button, a finger clutch button, and a hand sensor.

21. The multi-arm robotic surgical system as claimed in claim 20, wherein the hand gripper is configured to be grasped between thumb and index finger of left hand or right hand.

22. The multi-arm robotic surgical system as claimed in claim 20, wherein the pinch grip button is configured to control the closure and opening of a jaw of a surgical instrument.

23. The multi-arm robotic surgical system as claimed in claim 20, wherein the finger clutch button is configured to reorient the left-hand controller and the right-hand controller to a different space without compromising the position of the surgical instrument within the patient.

24. The multi-arm robotic surgical system as claimed in claim 20, wherein the hand sensor will maintain the position of the left-hand controller and the right-hand controller if left unattended by the surgeon.

25. The multi-arm robotic surgical system as claimed in claim 1, wherein the left-hand controller and the right-hand controller has specific rotational and translational motions corresponding to the motions of the plurality of surgical instruments.

26. The multi-arm robotic surgical system as claimed in claim 25, wherein the specific rotational motions of the left-hand controller and the right-hand controller include Roll, Pitch, and Yaw.

27. The multi-arm robotic surgical system as claimed in claim 26, wherein the Roll rotational motion of the hand gripper controls the rotation of surgical instrument along an axis 1.

28. The multi-arm robotic surgical system as claimed in claim 26, wherein the Pitch rotational motion of the hand gripper controls the rotation of the surgical instrument along an axis 2.

29. The multi-arm robotic surgical system as claimed in claim 26, wherein the Yaw rotational motion of the hand gripper controls the rotation of the surgical instrument along an axis 3.

30. The multi-arm robotic surgical system as claimed in claim 25, wherein the translation motions corresponding to the motions of the surgical instrument translate the surgical instrument in and out of the surgical field or up/down and left/right translation of the surgical instrument along a remote centre of motion (RCM).

31. The multi-arm robotic surgical system as claimed in claim 1, wherein the height of the 3D HD monitor and the left-hand controller and the right-hand controller is configured to be adjusted by the surgeon.

32. The multi-arm robotic surgical system as claimed in claim 1, wherein the position of foot pedal is configured to be adjusted up/down or in/out by the foot pedal controller.

33. The multi-arm robotic surgical system as claimed in claim 1, wherein the clutch of the foot pedal controller enables engaging/disengaging the left-hand controller and the right-hand controller for repositioning and engaging the plurality of surgical instruments.

34. The multi-arm robotic surgical system as claimed in claim 1, wherein the appropriate power signal provided to various cauterization surgical instruments out of the plurality of surgical instruments depends on the type of the surgical instrument.

35. The multi-arm robotic surgical system as claimed in claim 1, wherein a pre-operative 2D touch panel is provided for entering preoperative patient and surgical data by a patient side staff.

* * * * *